(12) United States Patent
Harichian et al.

(10) Patent No.: US 6,875,425 B2
(45) Date of Patent: *Apr. 5, 2005

(54) SKIN LIGHTENING AGENTS, COMPOSITIONS AND METHODS

(75) Inventors: Bijan Harichian, Warren, NJ (US); Michael James Barratt, Oak Ridge, NJ (US); Carol Annette Bosko, Oradell, NJ (US); Michael Tallman, Park Ridge, NJ (US)

(73) Assignee: Unilever Home & Personal Care USA, Greenwich, CT (US)

( * ) Notice: Subject to any disclaimer, the term of this patent is extended or adjusted under 35 U.S.C. 154(b) by 153 days.

This patent is subject to a terminal disclaimer.

(21) Appl. No.: 10/317,484

(22) Filed: Dec. 12, 2002

(65) Prior Publication Data

US 2004/0115145 A1 Jun. 17, 2004

(51) Int. Cl.[7] .................. A61K 7/42; A61K 7/44; A61K 7/00
(52) U.S. Cl. .................. 424/59; 424/60; 424/400; 424/401
(58) Field of Search .................. 424/59, 60, 70.1, 424/400, 401

(56) References Cited

U.S. PATENT DOCUMENTS

| | | |
|---|---|---|
| 4,959,393 A | 9/1990 | Torihara et al. |
| 5,468,472 A | 11/1995 | LaGrange et al. |
| 5,880,314 A | 3/1999 | Shinomiya et al. |
| 6,132,740 A | 10/2000 | Hu |
| 6,403,065 B1 | 6/2002 | Chevalier et al. |
| 2002/0155075 A1 | 10/2002 | Collington |

FOREIGN PATENT DOCUMENTS

| | | |
|---|---|---|
| DE | 20110355 | 10/2001 |
| EP | 0 623 339 | 11/1994 |
| EP | 1 134 207 A1 | 9/2001 |
| GB | 1 581 428 | 10/1980 |
| JP | 11-255638 | 9/1999 |
| JP | 2000327557 | 11/2000 |
| JP | 2001010925 | 1/2001 |
| SU | 1583407 A1 | 8/1990 |
| WO | 00/56702 | 9/2000 |

OTHER PUBLICATIONS

Int'l. Search Report no. PCT/EP 03/13642 dated Apr. 1, 2004—3pp.
Patent Abstracts of Japan vol. 1998, no. 04 abstract of JP 09 328411 (Mikimoto Pharmaceutical Co.) Dec. 22, 1997.
Lille, et al., *On Synthesis of 4–Substituted Alkyl Resorcins and Their IR Spectra*, Tr. Nauch–Issled., Inst. Slantsev 1969, No. 18:127–134—with translation.
Ballini et al., *Thioacetalization of Carbonyl Compounds by Zeolite HSZ–360 as a New, Effective Heterogeneous Catalyst, Synthetic Communications* 1999, 29(5), 767–772.
Dressler, Hans, *The Properties and Chemistry of Resorcinol, Resorcinol, Resorcinol its Uses and Derivatives*, Chapter 2, pp. 5–27, 1994.
U.S. Appl. No. 60/432,857, filed Dec. 12, 2002, Harichian et al., Novel Skin Lightening Agents, Compositions and Methods.
U.S. Appl. No. 10/314,627, filed Dec. 9, 2002, Harichian et al., Di–Substituted Resorcinols as Skin Lightening Agents.

*Primary Examiner*—Shelley A. Dodson
(74) *Attorney, Agent, or Firm*—Ellen Plotkin

(57) ABSTRACT

Cosmetic compositions and methods of skin lightening using compounds of formula I as skin lightening agents:

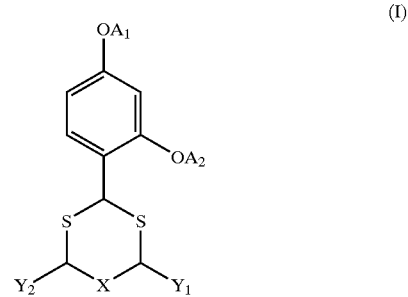

(I)

Wherein X represents Carbon, Nitrogen, Sulfur or Oxygen; each $A_1$ and/or $A_2$ independently is =H or COR, $CO_2R$, CONHR having the following formula A:

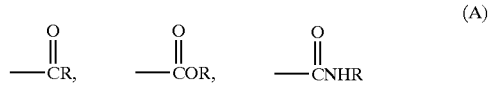

(A)

where R=$C_1$–$C_{18}$ saturated or unsaturated, linear or branched, hydrocarbon; and each $Y_1$ and/or $Y_2$ independently is $C_1$–$C_{18}$ saturated or unsaturated hydrocarbon or OZ, where Z=H or $COR^1$, $CO_2R^1$, $CONHR^1$ of formula B:

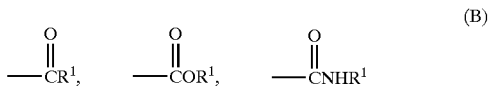

(B)

and where $R^1$=$C_1$–$C_{18}$ saturated or unsaturated, linear or branched, hydrocarbon.

16 Claims, No Drawings

SKIN LIGHTENING AGENTS, COMPOSITIONS AND METHODS

FIELD OF THE INVENTION

The invention relates to cosmetic methods of using 4-substituted resorcinol derivative compounds and cosmetic compositions including same, and more specifically, 1,3-dithiane resorcinol derivatives, as skin lightening agents.

BACKGROUND OF THE INVENTION

Many people are concerned with the degree of pigmentation of their skin. For example, people with age spots or freckles may wish such pigmented spots to be less pronounced. Others may wish to reduce the skin darkening caused by exposure to sunlight or to lighten their natural skin color. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new skin lightening agents, with improved overall effectiveness.

Resorcinol derivatives have cosmetic skin and hair benefits. Certain resorcinol derivatives, particularly 4-substituted resorcinol derivatives, are useful in cosmetic compositions for skin lightening benefits. Resorcinol derivatives are described in many publications, including Hu et al., U.S. Pat. No. 6,132,740; Collington et al., PCT Patent Application WO 00/56702; Bradley et al., European Patent Application EP 1 134 207; Shinomiya et al., U.S. Pat. No. 5,880,314; LaGrange et al., U.S. Pat. No. 5,468,472; Hiroaki et al., Japanese Patent Application JP11-255638 A2; Torihara et al., U.S. Pat. No. 4,959,393; and Japanese published patent applications JP 2001-010925 and JP2000-327557. Resorcinol derivatives are known compounds and can be readily obtained by various means, including by a method wherein a saturated carboxylic acid and resorcinol are condensed in the presence of zinc chloride and the resultant condensate is reduced with zinc amalgam/hydrochloric acid (Lille, et al., Tr. Nauch-Issled. Inst. Slantsev 1969, No. 18:127–134), or by a method wherein resorcinol and a corresponding alkyl alcohol are reacted in the presence of an alumina catalyst at a high temperature of from 200 to 400° C. (British Patent No. 1,581,428). Some of these compounds can be irritating to the skin.

Applicants have now discovered that the use of 1,3-dithiane resorcinols deliver skin lightening benefits. The general chemical formulas and structures of these compounds are discussed in more detail herein below. The 1,3-dithiane resorcinos have been found to be effective and possibly less irritating to the skin and have not been used for lightening skin.

SUMMARY OF THE INVENTION

The use of compounds of the general formula I, and compositions including same, delivers skin lightening benefits with potential reduced irritation. The present invention provides a cosmetic composition and method of skin lightening using in addition to a cosmetically acceptable vehicle, about 0.000001 to about 50% of a compound of formula I,

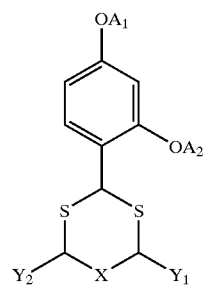

Where:
X=Carbon, Nitrogen, Sulfur or Oxygen; and
each $A_1$ and/or $A_2$ independently is =H or COR (acyl group), $CO_2R$, CONHR having the following formula A:

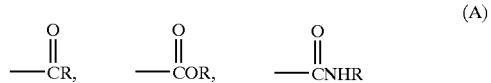

where R=$C_1$–$C_{18}$ saturated or unsaturated, linear or branched, hydrocarbon; and
each $Y_1$ and/or $Y_2$ independently is $C_1$–$C_{18}$ saturated or unsaturated hydrocarbon or OZ, where Z=H or $COR^1$, $CO_2R^1$, $CONHR^1$ of formula B:

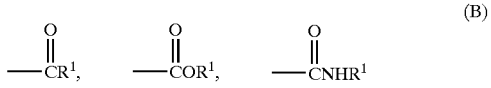

and where $R^1$=$C_1$–$C_{18}$ saturated or unsaturated, linear or branched, hydrocarbon.

In a preferred embodiment, each or both $A_1$ and/or $A_2$ represents H and each $Y_1$ and/or $Y_2$ represents H. In a more preferred embodiment, both $A_1$ and $A_2$ represent H, and both $Y_1$ and $Y_2$ represent H, so that the compound is of formula II as follows (with X defined as above with reference to formula I):

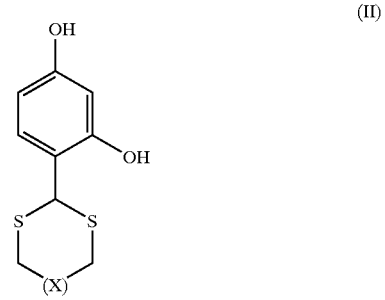

Optionally, the hydroxy groups may be further substituted by methods known in the art. For example, the one or both hydroxy groups may be esterified with any or a combination of the following acids: ferulic acid, vanillic acid, sebacic acid, azeleic acid, benzoic acid, caffeic acid, coumaric acid, salicylic acid, cysteine, cystine, lactic acid, and glycolic acid.

Further skin benefit agents may be included in the compositions useful for the inventive method. Organic and inorganic sunscreens, as well as perfumes, may also be included.

The inventive compositions and methods have effective skin lightening properties, may be less irritating to the skin, and are cost-effective.

DETAILED DESCRIPTION OF THE INVENTION

As used herein, the term "cosmetic composition" is intended to describe compositions for topical application to human skin.

The term "skin" as used herein includes the skin on the face, neck, chest, back, arms, axilla, hands, legs, and scalp.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

It should be noted that in specifying any range of concentration, any particular upper concentration can be associated with any particular lower concentration.

For the avoidance of doubt the word "comprising" is intended to mean including but not necessarily consisting of or composed of. In other words the listed steps or options need not be exhaustive.

Skin Lightening Agents

The invention is concerned with the use of compounds of general formula I, shown below, and compositions including same, as skin lightening agents. A particular advantage of the inventive compositions and methods is that compounds of general formula I can be less irritating to the skin than other, known, skin lightening compounds. The present invention provides a cosmetic composition and method of skin lightening using in addition to a cosmetically acceptable vehicle, about 0.000001 to about 50% of a compound of formula I,

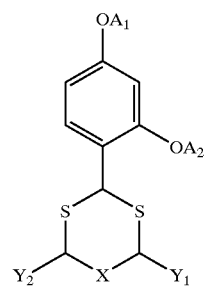

(I)

Where:
X=Carbon, Nitrogen, Sulfur or Oxygen; and
each $A_1$ and/or $A_2$ independently is =H or COR (acyl group), $CO_2R$, CONHR, the latter three having the following formula A, respectively:

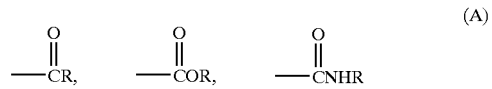

(A)

where R=$C_1$–$C_{18}$ saturated or unsaturated, linear or branched, hydrocarbon; and each $Y_1$ and/or $Y_2$ independently is $C_1$–$C_{18}$ saturated or unsaturated hydrocarbon or OZ, where Z=H or $COR^1$, $CO_2R^1$, $CONHR^1$ of formula B:

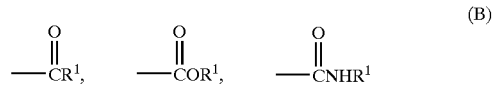

(B)

and where $R^1$=$C_1$–$C_{18}$ saturated or unsaturated, linear or branched, hydrocarbon.

In a preferred embodiment, each or both $A_1$ and/or $A_2$ represents OH and each or both $Y_1$ and/or $Y_2$ represents H. In a more preferred embodiment, both $A_1$ and $A_2$ represent OH and both $Y_1$ and $Y_2$ represent H, so that the compound is of formula II as follows (with X defined as above with reference to formula I):

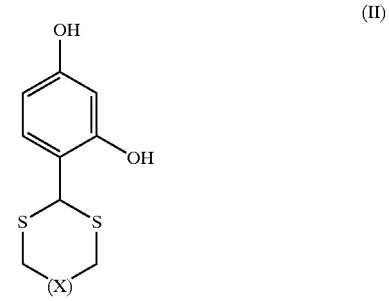

(II)

In the compound of general formula II, optionally, the hydroxy groups (the hydrogen on one or both of the OH-groups) may be further substituted by methods known in the art. For example, one or both hydroxy groups may be esterified with any or a combination of the following acids: ferulic acid, vanillic acid, sebacic acid, azaleic acid, benzoic acid, caffeic acid, coumaric acid, salicylic acid, cysteine, cystine, lactic acid, and glycolic acid.

Procedure for Making 1,3-dithiane Resorcinol

In a most preferred embodiment, both $A_1$ and $A_2$ represent H, both $Y_1$ and $Y_2$ represent H, and X represents Carbon. This most preferred embodiment, referred to herein as 1,3-dithiane resorcinol, may be prepared by reaction of 2,4-dihydroxy benzaldehyde and 1,3-Dimercaptopropane (Both starting materials are available from Yick-Vic Chemicals & Pharmaceuticals (HK) Ltd/Hong Kong), denoted by the following formula III and catalyzed by an acid catalyst. Suitable catalysts include but are not limited to methane sulfonic acid, p-toluene sulfonic acid, $H_2SO_4$ (sulfuric acid), HCl (hydrochloric acid) and acidic resins.

A three necked flask equipped with a Dean-Stark apparatus, an additional funnel and a condenser is charged with 2,4-dihydroxy benzaldehyde (1 equ.). To this was added toluene (500 ml) and a catalytic amount of p-toluene sulfonic acid. The mixture was heated at 120 C. One equivalent of 1,3-dithiopropane in toluene (100 ml) was added dropwise to the mixture. The mixture was stirred at reflux up to 12 hrs. The solvent was removed on a rotavap and the expected product was isolated. The structure of the dithiane was confirmed using Mass spectroscopy, NMR and IR.

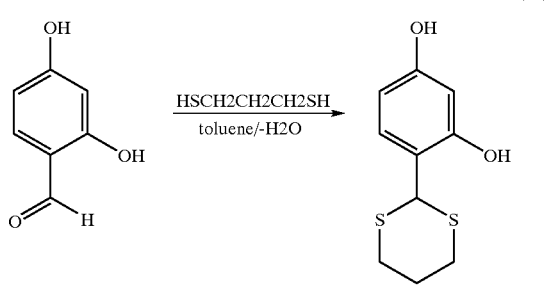

The inventive compositions and methods have effective skin lightening properties, may be less irritating to the skin than other skin lightening actives, and are relatively easy to manufacture and cost-effective.

The compositions generally contain about 0.000001 to about 50% of compounds of general formula I, II, and/or. Compounds of general formula II are preferred, and compounds of formula III are most preferred. The amount of the inventive compound is preferably in the range of about 0.00001% to about 10%, more preferably about 0.001 to about 7%, most preferably from 0.01 to about 5%, of the total amount of cosmetic composition. Further skin benefit agents may be included in the compositions useful for the inventive method. Organic and inorganic sunscreens, as well as fragrances, may also be included.

Optional Skin Benefit Agents

Preferred cosmetic compositions are those suitable for the application to human skin according to the method of the present invention, which optionally, but preferably, include a skin benefit agent in addition to a compound of general formula I.

Suitable additional skin benefit agents include anti-aging, wrinkle-reducing, skin whitening, anti-acne, and sebum reduction agents. Examples of these include alpha-hydroxy acids, beta-hydroxy acids, polyhydroxy acids, hydroquinone, t-butyl hydroquinone, niacinamide, Vitamic C derivatives, dioic acids (e.g., malonic acid, sebacic acid), linoleic acid, retinoids, and resorcinol derivatives other than compound of general formula I of the present invention.

Cosmetically Acceptable Carrier

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferably oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers.

These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterol esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Optional Components

In the cosmetic compositions of the invention, there may be added various medically effective ingredients, such as allantoin, a placenta extract; other thickeners, plasticizers; calamine; pigments; antioxidants; and chelating agents; as well as additional sunscreens such organic sunscreens, typical of which are PARSOL 1789 and PARSOL MCX.

Other adjunct minor components may also be incorporated into the cosmetic compositions. These ingredients may include coloring agents, opacifiers, and perfumes. Amounts of these other adjunct minor components may range anywhere from 0.001% up to 20% by weight of the composition.

Sunscreens

For use as sunscreen, metal oxides may be used alone or in mixture and/or in combination with organic sunscreens. Examples of organic sunscreens include but are not limited those set forth in the table below:

TABLE 1

Typical Organic Sunscreens

| CTFA Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The amount of the organic sunscreens in the cosmetic composition is preferably in the range of about 0.1 wt % to about 10 wt %, more preferably about 1 wt % to 5 wt %.

Preferred organic sunscreens are PARSOL MCX and Parsol 1789, due to their effectiveness and commercial availability.

Perfumes

Perfumes are fragrance compositions that are mixtures of components providing, usually, a pleasing sense of smell. Terpenes and terpene derivatives are often an important component of fragrances. Fragrance terpenes and derivatives are described in Bauer, K., et al., Common Fragrance and Flavor Materials, VCH Publishers (1990).

Terpenes and derivatives that may preferably be incorporated in the inventive cosmetic compositions are divided into three classes, including acyclic terpenoids, cyclic terpenoids, and cycloaliphatic compounds that are structurally related to terpenoids.

Terpene derivatives within each of the three classes include alcohols, ethers, aldehydes, acetals, acids, ketones, esters, and terpene compounds that contain heteroatoms such as nitrogen or sulfur.

Examples of terpenes and derivative that may be incorporated in the cosmetic compositions of the present invention are set forth in the tables below:

TABLE 2

Acyclic Terpenes and Derivatives

HYDROCARBONS

Myrcene
Ocimene
beta-Farnesene

ALCOHOLS

| | |
|---|---|
| Dihydromyrcenol | (2,6-dimethyl-7-octen-2-ol) |
| Geraniol | (3,7-dimethyl-trans-2,6-octadien-1-ol) |
| Nerol | (3,7-dimethyl-cis-2,6-octadien-1-ol) |
| Linalool | (3,7-dimethyl-1,6-octadien-3-ol) |
| Myrcenol | (2-methyl-6-methylene-7-octen-2-ol) |
| Lavandulol | |
| Citronellol | (3,7-dimethyl-6-octen-1-ol) |
| Trans-trans-Farnesol | (3,7,11-trimethyl-2,6,10-dodecatrien-1-ol) |
| Trans-Nerolidol | (3,7,11-trimethyl-1,6,10-dodecatrien-3-ol) |

ALDEHYDES
AND ACETALS

| | |
|---|---|
| Citral | (3,7-dimethyl-2,6-octadien-1-al) |
| Citral diethyl acetal | (3,7-dimethyl-2,6-octadien-1-al diethyl acetal) |
| Citronellal | (3,7-dimethyl-6-octen-1-al) |
| Citronellyloxyacetaldehyde | |
| 2,6,10-Trimethyl-9-undecenal | |

KETONES

Tagetone
Solanone
Geranylacetone   (6,10-dimethyl-5,9-undecadien-2-one)

ACIDS AND ESTERS

Cis-Geranic acid
Citronellic acid
Geranyl Esters, including Geranyl formate,
Geranyl acetate, Geranyl propionate,
Geranyl isobutyrate, Geranyl isovalerate
Neryl Esters, including Neryl acetate
Linalyl Esters, including Lynalyl formate,
Linalyl acetate, Linalyl propionate,
Linalyl butyrate, Linalyl isobutyrate,
Lavandulyl Esters, including Lavendulyl acetate
Citronellyl Esters, including Citronellyl formate,
Citronellyl acetate, Citronellyl
propionate, Citronellyl isobutyrate,
Citronellyl isovalerate, Citronellyl tiglate

NITROGEN CONTAINING UNSATURATED TERPENE DERIVATIVES

Cis-Geranic acid nitrile
Citronellic acid nitrile

TABLE 3

Cyclic Terpenes and Derivatives

HYDROCARBONS

| | |
|---|---|
| Limonene | (1,8-p-menthadiene) |
| Alpha-Terpinene | |
| Gamma-Terpinene | (1,4-p-menthadiene) |
| Terpinolene | |

TABLE 3-continued

Cyclic Terpenes and Derivatives

| | |
|---|---|
| Alpha-Phellandrene | (1,5-p-menthadiene) |
| Beta-Phellandrene | |
| Alpha-Pinene | (2-pinene) |
| Beta-Pinene | (2(10)-pinene) |
| Camphene | |
| 3-Carene | |
| Caryophyllene | |
| (+)-Valencene | |
| Thujopsene | |
| Alpha-Cedrene | |
| Beta-Cedrene | |
| Longifolene | |

ALCOHOLS
AND ETHERS

| | |
|---|---|
| (+)-Neoiso-isopulegol | |
| Isopulegol | (8-p-menten-3-ol) |
| Alpha-Terpineol | (1-p-menten-8-ol) |
| Beta-Terpineol | |
| Gamma-Terpineol | |
| Delta-Terpineol | |
| 1-Terpinen-4-ol | (1-p-menten-4-ol) |

ALDEHYDES
AND KETONES

| | |
|---|---|
| Carvone | (1,8-p-mantadien-6-one) |
| Alpha-Ionone | ($C_{13}H_{20}O$) |
| Beta-Ionone | ($C_{13}H_{20}O$) |
| Gamma-Ionone | ($C_{13}H_{20}O$) |
| Irone, alpha-, beta-, gamma- | ($C_{14}H_{22}O$) |
| n-Methylionone, alpha-, beta-, gamma- | ($C_{14}H_{22}O$) |
| Isomethylionone, alpha-, beta-, gamma- | ($C_{14}H_{22}O$) |
| Allylionone | ($C_{16}H_{24}O$) |
| Pseudoionone | |
| n-Methylpseudoionone | |
| Isomethylpseudoionone | |
| Damascones | 1-(2,6,6-trimethylcyclohexenyl)-2-buten-1-ones |
| Including beta-Damascenone | 1-(2,6,6-trimethyl-1,3-cyclohadienyl)-2-buten-1-one |
| Nootkatone | 5,6-dimethyl-8-isopropenylbicyclo[4.4.0]-1-decen-3-one |
| Cedryl methyl ketone | ($C_{17}H_{26}O$) |

ESTERS

| | |
|---|---|
| Alpha-Terpinyl acetate | (1-p-menthen-8-yl acetate) |
| Nopyl acetate | (−)-2-(6,6-dimethylbicyclo[3.1.1]hept-2-en-2-yl)ethyl acetate |
| Khusymil acetate | |

TABLE 4

Cycloaliphatic Compounds Structurally Related to Terpenes

ALCOHOLS 5-(2,2,3-Trimethyl-3-cyclopenten-1-yl)-3-methylpentan-2-ol

ALDEHYDES 2,4-Dimethyl-3-cyclohexene carboxaldehyde
4-(4-Methyl-3-penten-1-yl)-3-cyclohexene carboxaldehyde
4-(4-Hydroxy-4-methypentyl)-3-cyclohexene carboxaldehyde

KETONES

| | |
|---|---|
| Civetone | |
| Dihydrojasmone | (3-methyl-2-pentyl-2-cyclopenten-1-one) |
| Cis-Jasmone | 3-methyl-2-(2-cis-penten-1-yl)-2-cyclopenten-1-one |
| 5-Cyclohexadecen-1-one | |

TABLE 4-continued

Cycloaliphatic Compounds Structurally Related to Terpenes 2,3,8,8-Tetramethyl-1,2,3,4,5,6,7,8-octahydro-2-napthalenyl methyl
ketone 3-methyl-2-cyclopenten-2-ol-1-one

ESTERS 4,7-Methano-3a,4,5,6,7,7a-hexahydro-5-(or 6)-indenyl acetate
Allyl 3-cyclohexylpropionate
Methyl dihydrojasmonate methyl (3-oxo-pentylcyclopentyl)acetate Preferably, the amount of terpenes and derivatives in the cosmetic composition is in the range of about 0.000001% to about 10%, more preferably about 0.00001% to about 5 wt %, most preferably about 0.0001% to about 2%.

Use of the Composition

The method according to the invention is intended primarily as using a personal care product for topical application to human skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The cosmetic composition useful for the method of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. When the composition is a solid or semi-solid stick, it may be packaged in a suitable container for manually or mechanically pushing out or extruding the composition.

The invention accordingly also-provides a closed container containing a cosmetically acceptable composition as herein defined.

The following examples are by way of example, not by way of limitation, of the principles of the present invention, to illustrate the best mode of carrying out the invention.

EXAMPLE 1

The following compound, referred to herein as di-thiane resorcinol, prepared by the method described above, was used throughout the examples that follow:

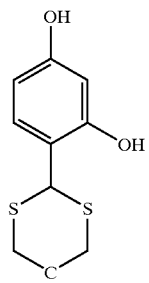

EXAMPLE 2

Cosmetic compositions within the scope of the invention were prepared.

A base formulation shown in Table 3, below, was made by heating phase A ingredients to 70 to 85° C. with stirring. Phase B ingredients were heated in a separate container to 70 to 85° C. with stirring. Then, phase A was added into phase B while both phases were kept at 70 to 85° C. The mixture was stirred for at least 15 minutes at 70 to 85° C., then cooled.

A base formulation is shown in the table below.

TABLE 5

| Ingredients | a % wt. | b % wt. | Phase |
|---|---|---|---|
| Isostearyl Palmitate | 6.00 | 6.00 | A |
| C12–C15 Alkyl Octanoate | 3.00 | 3.00 | A |
| PEG-100 Stearate | 2.00 | 2.00 | A |
| Glyceryl Hydroxystearate | 1.50 | 1.50 | A |
| Stearyl Alcohol | 1.50 | 1.50 | A |
| Stearic acid | 3.00 | 4.00 | A |
| TEA, 99% | 1.20 | 1.20 | B |
| Dimethicone | 1.00 | 1.00 | A |
| Sorbitan Monostearate | 1.00 | 1.00 | A |
| Magnesium Aluminum Silicate | 0.60 | 0.60 | B |
| Vitamin E acetate | 0.10 | 0.10 | A |
| Cholesterol | 0.50 | 0.50 | A |
| Simethicone | 0.01 | 0.01 | B |
| Xanthan gum | 0.20 | 0.20 | B |
| Hydroxyethylcellulose | 0.50 | 0.50 | B |
| Propylparaben | 0.10 | 0.10 | B |
| Disodium EDTA | 0.05 | 0.05 | B |
| Butylated hydroxytolene | 0.05 | 0.05 | B |
| Di-Thiane Resorcinol) | 0.05 | 2.00 | B |
| Niacinamide | 1.00 | 1.00 | B |
| Metal oxide | 2.50 | 5.00 | B |
| Methylparaben | 0.15 | 0.15 | B |
| Water | BAL* | BAL* | B |
| Total | 100.00 | 100.00 | B |

*BAL means Balance.

EXAMPLE 3

Additional cosmetic compositions within the scope of the invention were prepared.

TABLE 6

|  | Wt % | Phase |
|---|---|---|
| water, DI | BALANCE | A |
| disodium EDTA | 0.05 | A |
| magnesium aluminum silicate | 0.6 | A |
| methyl paraben | 0.15 | A |

TABLE 6-continued

|  | Wt % | Phase |
|---|---|---|
| simethicone | 0.01 | A |
| butylene glycol 1,3 | 3.0 | A |
| hydroxyethylcellulose | 0.5 | A |
| glycerine, USP | 2.0 | A |
| xanthan gum | 0.2 | A |
| triethanolamine | 1.2 | B |
| stearic acid | 3.0 | B |
| propyl paraben NF | 0.1 | B |
| glyceryl hydroxystearate | 1.5 | B |
| stearyl alcohol | 1.5 | B |
| isostearyl palmitate | 6.0 | B |
| C12–15 alcohols octanoate | 3.0 | B |
| dimethicone | 1.0 | B |
| cholesterol NF | 0.5 | B |
| sorbitan stearate | 1.0 | B |
| Micronized titanium dioxide | 5.0 | C |
| tocopheryl acetate | 0.1 | B |
| PEG-100 stearate | 2.0 | B |
| sodium stearoyl lactylate | 0.5 | B |
| hydroxycaprylic acid | 0.1 | C |
| Di-Thiane Resorcinol | 10.0 | C |
| PARSOL MCX | 2.4 | C |
| alpha-bisabolol | 0.2 | C |

The composition of Example 3, was prepared as follows:
1. Heat Phase A to 80° C.
2. Heat Phase B to 75° C. in a separate container
3. Add B to A and mix with heat off for 30 min.
4. At 50° C. add Phase C and mix for 10 min.

EXAMPLES 4–11

A set of additional compositions useful in the methods of the present invention were prepared within the scope of the present invention and are listed in the table below.

TABLE 7

| | | Examples (wt. %) | | | | | | | |
|---|---|---|---|---|---|---|---|---|---|
| Ingredients | Phase | 4 acid soap base | 5 | 6 | 7 | 8 | 9 | 10 | 11 |
| Stearic acid | A | 17.9 | 17.9 | 17.9 | 17.9 | 17.9 | 17.9 | 17.9 | 17.9 |
| Sodium cetearyl sulfate* (emulsifier) | A | | 2.2 | | 1 | 1.5 | 2 | 3 | 2 |
| Myrj 59* (emulsifier) | A | | | 2 | 2 | 2 | 2 | 2 | 1 |
| Span 60* (emulsifiers) | A | | | 2 | 2 | 2 | 2 | 2 | 1 |
| Di-thiane Resorcinol | B | 0.05 | 0.05 | 2.0 | 2.0 | 3.5 | 3.5 | 5.0 | 10.0 |
| Micronized Zinc Oxide | B | | 2.50 | 5.00 | 5.00 | 2.50 | 2.50 | 5.00 | 2.50 | 5.00 |
| KOH, 22% (form in situ soap with stearic acid) | | 2.20 | | | | | | | |
| Octyl methoxycinnamate | | | 2.50 | | | 2.50 | 2.50 | | 2.50 |
| Water | B | | BAL | BAL | BAL | BAL | BAL | BAL | BAL |
| Glycerin | B | 1 | 1 | 1 | 1 | 1 | 1 | 1 | 1 |

EXAMPLE 12

Mushroom Tyrosinase Assay

Mushroom tyrosinase inhibition is indicative of reduction in melanin synthesis, thereby showing skin lightening effect. This experiment shows the efficacy of resorcinol derivatives of the present invention.

Into each well of a 96-well plate, 150 microliters of phosphate buffer (100 mM, pH 7.0), 10 microliters of L-DOPA (L-3,4-Dihydroxyphenylalanine, 10 mM), and 20 microliters of skin lightening agent (dissolved in ethanol, which is the control) were added. Following an initial measurement of background absorbency at 475-nm, 20 microliters of mushroom tyrosinase (Sigma T-7755; 6050 units/ml) was added and incubated at room temperature.

Absorbency is read at 475-nm over the following time points: 0, 2, 4, and 6.5 minutes. The data is plotted as 475-nm absorbency vs. time (minutes) and the slope of the line is calculated (ΔAbs 475nm/min). Values are expressed as the percentage of the respective untreated ethanol control reaction.

$$\% \text{ of Control} = \frac{\text{(Reaction rate for treated reaction)}}{\text{(Reaction rate for untreated control)}} \times 100\%$$

TABLE 8

Mushroom Tyrosinase Assay Results

| Compound | Concentration | % of Control (Melanin Synthesis) |
|---|---|---|
| 4-Ethyl Resorcinol | 0.1 uM | 73 |
| | 1 uM | 46 |
| | 10 uM | 31 |
| | 100 uM | 21 |
| 1,3-di-Thiane Resorcinol | 0.1 uM | 87 |
| | 1 uM | 57 |
| | 10 uM | 48 |
| | 100 uM | 47 |

TABLE 8-continued

Mushroom Tyrosinase Assay Results

| Compound | Concentration | % of Control (Melanin Synthesis) |
|---|---|---|
| Resorcinol | 0.1 uM | 97 |
|  | 1 uM | 98 |
|  | 10 uM | 98 |
|  | 100 uM | 100 |

The data show that the inventive compounds are substantially as effective or slightly less effective than 4-ethyl resorcinol, both compounds having good skin lightening effects. An advantage of the inventive compounds is that they are relatively easy and cost-effective to manufacture. Resorcinol, which has only a single hydrogen at the 4-position, does not display activity in the above assay and does not yield a skin lightening benefit.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of skin lightening comprising applying to the skin a composition comprising:
   a. about 0.000001 to about 50% of a compound of general formula I

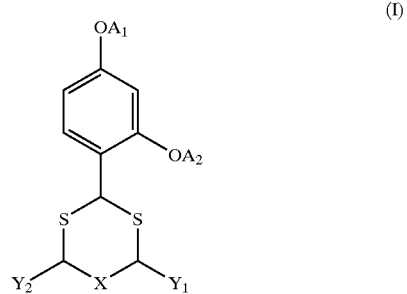

(I)

Wherein
   X=Carbon, Nitrogen, Sulfur or Oxygen;
   each $A_1$ and/or $A_2$ independently is =H, COR, $CO_2R$, CONHR where R=$C_1$–$C_{18}$ saturated or unsaturated hydrocarbon; and
   each $Y_1$ and/or $Y_2$ independently is H, $C_1$–$C_{18}$ saturated or unsaturated hydrocarbon, or OZ, where Z=H, $COR^1$, $CO_2R^1$, $CONHR^1$ and where $R^1$=$C_1$–$C_{18}$ saturated or unsaturated hydrocarbon; and
   b. a cosmetically acceptable carrier.

2. The method of claim 1, wherein said compound of general formula I is esterified with an acid selected from the group consisting of ferulic acid, vanillic acid, sebacic acid, azaleic acid, benzoic acid, caffeic acid, coumaric acid, salicylic acid, cysteine, cystine, lactic acid, glycolic acid and mixtures thereof.

3. The method of claim 1, wherein said composition further comprises a sunscreen.

4. The method of claim 3, wherein said sunscreen is a micronized metal oxide.

5. The method of claim 1, wherein said compound is a compound of formula II:

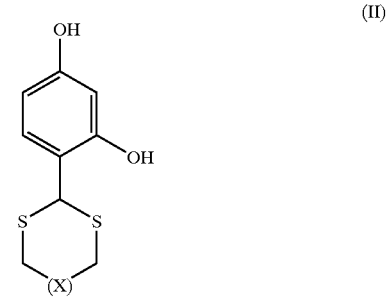

(II)

wherein X=Carbon, Nitrogen, Sulfur or Oxygen.

6. The method of claim 1, wherein said composition further comprises a fragrance.

7. The cosmetic method according to claim 1, wherein said composition further comprises a skin benefit agent selected from the group consisting of alpha-hydroxy acids, beta-hydroxy acids, polyhydroxy acids, hydroquinone, t-butyl hydroquinone, niacinamide, Vitamin C derivatives, dioic acids, linoleic acid, retinoids, resorcinol derivatives, and mixtures thereof.

8. The cosmetic method of claim 1, wherein said composition further comprises an organic sunscreen selected from the group consisting of Benzophenone-3, Benzophenone-4, Benzophenone-8, DEA, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane (PARSOL 1789),Etocrylene, and mixtures thereof.

9. A cosmetic composition comprising:
   a. about 0.000001 to about 50% of a compound of general formula I

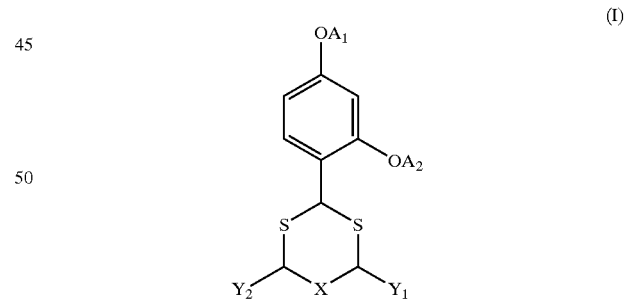

(I)

Wherein
   X=Carbon, Nitrogen, Sulfur or Oxygen;
   each $A_1$ and/or $A_2$ independently is =H, COR, $CO_2R$, CONHR where R=$C_1$–$C_{18}$ saturated or unsaturated hydrocarbon; and
   each $Y_1$ and/or $Y_2$ independently is H, $C_1$–$C_{18}$ saturated or unsaturated hydrocarbon, or OZ, where Z=H, $COR^1$, $CO_2R^1$, $CONHR^1$ and where $R^1$=$C_1$–$C_{18}$ saturated or unsaturated hydrocarbon; and
   b. a cosmetically acceptable carrier.

10. The cosmetic composition of claim 9, wherein said compound is a compound of general formula II:

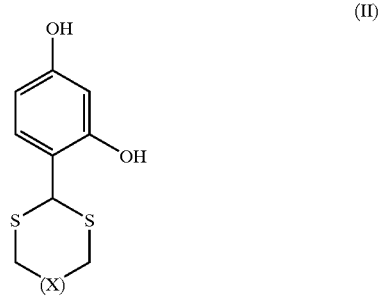

wherein X=Carbon, Nitrogen, Sulfur or Oxygen.

11. The cosmetic composition of claim 9, wherein said compound comprises about 0.00001% to about 10% of said composition.

12. The cosmetic composition of claim 9, wherein said compound comprises about 0.001% to about 7% of said composition.

13. The cosmetic composition of claim 9, wherein said compound comprises about 0.01% to about 5% of said composition.

14. The cosmetic composition of claim 9, further comprising a sunscreen.

15. The cosmetic composition of claim 14, wherein said sunscreen is a micronized metal oxide.

16. The cosmetic composition of claim 10, wherein the hydroxy groups of said compound of general formula II are esterified with an acid selected from the group consisting of ferulic acid, vanillic acid, sebacic acid, azaleic acid, benzoic acid, caffeic acid, coumaric acid, salicylic acid, cysteine, cystine, lactic acid, glycolic acid and mixtures thereof.

* * * * *